US011526991B2

United States Patent
Ito et al.

(10) Patent No.: US 11,526,991 B2
(45) Date of Patent: Dec. 13, 2022

(54) MEDICAL IMAGE PROCESSING APPARATUS, AND MEDICAL IMAGING APPARATUS

(71) Applicant: Hitachi, Ltd., Tokyo (JP)

(72) Inventors: Nao Ito, Tokyo (JP); Yoshimi Noguchi, Tokyo (JP); Tomofumi Nishiura, Tokyo (JP); Maki Kuwayama, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 160 days.

(21) Appl. No.: 17/203,952

(22) Filed: Mar. 17, 2021

(65) Prior Publication Data

US 2021/0366120 A1 Nov. 25, 2021

(30) Foreign Application Priority Data

May 25, 2020 (JP) .............................. JP2020-090860

(51) Int. Cl.
*G06T 7/00* (2017.01)
*G06K 9/62* (2022.01)
(Continued)

(52) U.S. Cl.
CPC ............ *G06T 7/0016* (2013.01); *A61B 8/085* (2013.01); *A61B 8/0825* (2013.01);
(Continued)

(58) Field of Classification Search
CPC . G06T 7/0016; G06T 7/11; G06T 7/70; G06T 2207/10132; G06T 2207/20084;
(Continued)

(56) References Cited

U.S. PATENT DOCUMENTS

2002/0177779 A1* 11/2002 Adler .................... A61B 5/743
128/923
2011/0216951 A1* 9/2011 Ye ........................ G06T 7/0012
382/128
(Continued)

FOREIGN PATENT DOCUMENTS

EP          2 085 019       *   8/2009
JP         2002-325762     *  11/2002
(Continued)

OTHER PUBLICATIONS

Machine translation for JP 2002-325762 (Year: 2002).*
(Continued)

*Primary Examiner* — Qian Yang

(74) *Attorney, Agent, or Firm* — Mattingly & Malur, PC

(57) ABSTRACT

In medical examination of breast cancer, a lesion computer-aided detection is performed in real time and with high accuracy, and a burden on a medical worker is reduced. A medical image processing apparatus that processes a medical image includes: a detection unit configured to detect a lesion candidate region; a validity evaluation unit configured to evaluate validity of the lesion candidate region by using a normal tissue region corresponding to the detected lesion candidate region; and a display unit configured to determine display content to a user by using an evaluation result.

15 Claims, 19 Drawing Sheets

(51) Int. Cl.
  *G06T 7/70* (2017.01)
  *A61B 8/08* (2006.01)
  *G06T 7/11* (2017.01)
  *G06V 10/22* (2022.01)
  *G06V 10/40* (2022.01)
  *G06V 10/75* (2022.01)

(52) U.S. Cl.
  CPC .............. *G06K 9/6262* (2013.01); *G06T 7/11* (2017.01); *G06T 7/70* (2017.01); *G06V 10/22* (2022.01); *G06V 10/40* (2022.01); *G06V 10/751* (2022.01); *G06T 2207/10132* (2013.01); *G06T 2207/20084* (2013.01); *G06T 2207/30068* (2013.01); *G06T 2207/30096* (2013.01); *G06V 10/759* (2022.01); *G06V 2201/03* (2022.01)

(58) Field of Classification Search
  CPC . G06T 2207/30068; G06T 2207/30096; A61B 8/0825; A61B 8/085; A61B 8/5223; A61B 8/5215; G06K 9/6262; G06V 10/22; G06V 10/40; G06V 10/751; G06V 10/759; G06V 2201/03; G06V 10/764; G06V 10/82
  See application file for complete search history.

(56) References Cited

U.S. PATENT DOCUMENTS

| | | | |
|---|---|---|---|
| 2013/0131507 A1* | 5/2013 | Salazar-Ferrer | A61B 6/5217 600/431 |
| 2015/0230773 A1 | 8/2015 | Cho et al. | |
| 2019/0089895 A1* | 3/2019 | Kono | H04N 5/23264 |
| 2019/0236782 A1* | 8/2019 | Amit | G16H 50/30 |

FOREIGN PATENT DOCUMENTS

| JP | 2015-154918 A | 8/2015 |
|---|---|---|
| JP | 2018-190132 A | 11/2018 |

OTHER PUBLICATIONS

Moon et al., "Tumor detection in automated breast ultrasound images using quantitative tissue clustering", Medical Physics, vol. 41, No. 4 (Year: 2014).*

Yap et al. "Automated Breast Ultrasound Lesions Detection Using Convolutional Neural Networks", IEEE Journal of Biomedical and Health Informatics, vol. 22, No. 4, Jul. 2018 (Year: 2018).*

Suzuki, "Pixel-Based Machine Learning in Medical Imaging", International Journal of Biomedical Imaging vol. 2012, Article ID 792079 (Year: 2012).*

* cited by examiner

210

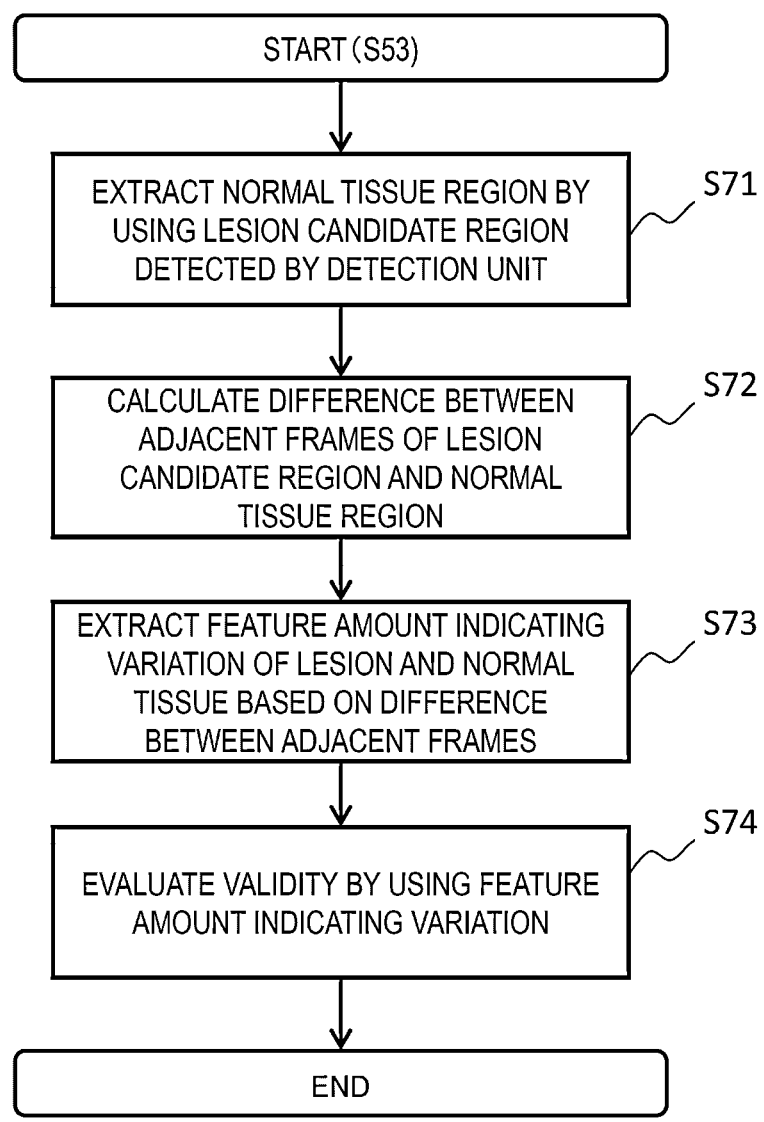

MEDICAL IMAGE PROCESSING APPARATUS, AND MEDICAL IMAGING APPARATUS

CROSS-REFERENCE TO RELATED APPLICATION

The present application claims priority from Japanese application JP 2020-090860, filed on May 25, 2020, the contents of which is hereby incorporated by reference into this application.

BACKGROUND OF THE INVENTION

1. Field of the Invention

The present invention relates to a lesion detection technique in a medical image diagnosis apparatus, and more particularly, to reduction of erroneous detection.

2. Description of the Related Art

In recent medical examination of breast cancer, in addition to mammography in related art, medical examination performed by an ultrasonic diagnosis apparatus is being performed in combination. Since it is necessary to interpret a large amount of ultrasonic images in ultrasonic examination and a burden on a medical worker is large, development of a computer-aided detection (CADe) performed by a computer is expected.

Since the breast ultrasonic image exhibits various appearances depending on an age of a subject, experience of an examiner, types of imaging apparatus, and the like in addition to types of lesions, detection difficulty is high among medical images. In particular, since a region showing a lesion is also present in normal tissue, erroneous detection tends to occur in many cases. In order to prevent a decrease in medical examination efficiency of an examiner, it is important to reduce erroneous detection of a machine when CADe is applied to a breast ultrasonic image.

As a general technique for reducing the erroneous detection in object detection, JP-A-2018-1901321 discloses a technique for specifying erroneous detection by using a difference between a foreground and a background and a variation amount of an aspect ratio of a detection rectangle. Further, as a technique for reducing the erroneous detection of a lesion in a breast ultrasonic image, JP-A-2015-154918 discloses a technique for detecting a lesion candidate region, grasping an anatomical structure in a breast, and determining whether there is a value of performing medical diagnosis on a detection result based on a relationship between the lesion candidate region and the anatomical structure.

In the method of reducing the erroneous detection based on the background difference described in JP-A-2018-190132, a region other than the foreground in the image is used as a background region. However, since a mammary gland is present only in a specific region in the breast ultrasonic image, it is difficult to determine the erroneous detection based on a difference between a region of a lesion of the detected mammary gland and the other region, and it is difficult to appropriately reduce the erroneous detection. In addition, the breast ultrasonic image is complicated and unclear, and it is considered that the analysis of an anatomical structure as disclosed in JP-A-2015-154918 requires a high processing cost, and thus real-time computer-aided detection is difficult.

SUMMARY OF THE INVENTION

The invention determines a normal tissue region corresponding to a detected lesion candidate region in an analysis target image in consideration of structural features of lesion tissue and normal tissue around the lesion tissue, and evaluates validity of the lesion candidate region by using information of the determined normal tissue region.

That is, a medical image processing apparatus of the invention includes: a detection unit configured to detect a lesion candidate region; and a validity evaluation unit configured to evaluate validity of the lesion candidate region by using a normal tissue region corresponding to the detected lesion candidate region.

For example, the medical image processing apparatus of the invention includes an image processing unit configured to process a medical image acquired by a medical image imaging apparatus. The image processing unit includes a detection unit configured to detect a lesion candidate region from the medical image, and a validity evaluation unit configured to evaluate validity of a detection result of the detection unit. The validity evaluation unit includes a normal tissue extraction unit configured to extract a normal tissue region from the medical image by using position information of the lesion candidate region detected by the detection unit, and a feature extraction unit configured to calculate a variation feature amount indicating a difference between features of the lesion candidate region and the normal tissue region, and evaluates validity of the detection result by using the variation feature amount calculated by the feature extraction unit.

A medical imaging apparatus according to the invention includes: an imaging unit configured to acquire a medical image; and an image processing unit configured to analyze the medical image acquired by the imaging unit. The image processing unit has a configuration of the medical image processing apparatus described above. The medical imaging apparatus is, for example, an ultrasonic imaging apparatus.

According to the invention, it is possible to reduce erroneous detection in a lesion detection in a medical image and to improve medical examination efficiency of an operator.

BRIEF DESCRIPTION OF THE DRAWINGS

FIG. 3 is a diagram showing a configuration example in which the ultrasonic imaging apparatus and an image processing apparatus are connected to each other via a network or the like.

FIG. 7 is a diagram showing a flow of processing of the validity evaluation unit according to the first embodiment.

DESCRIPTION OF THE PREFERRED EMBODIMENTS

Figure 1:
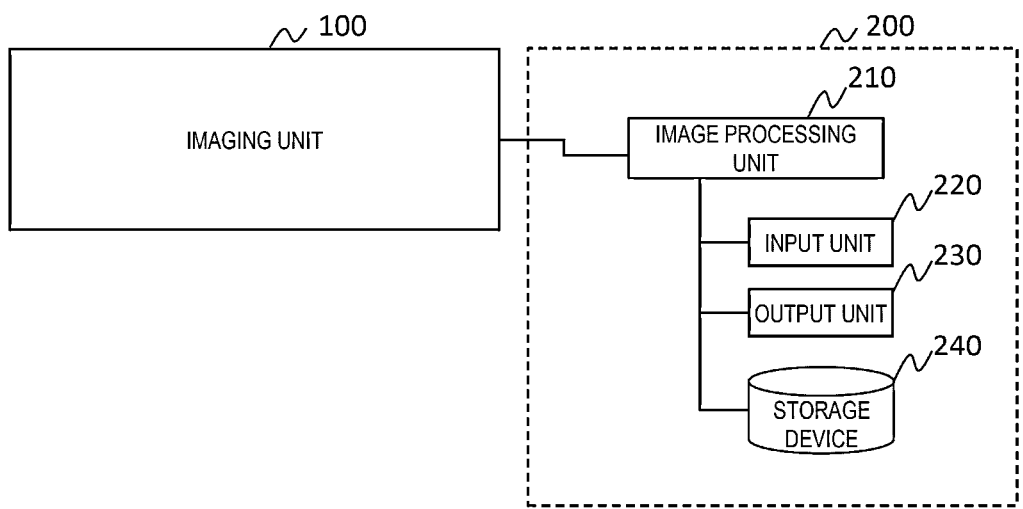
FIG. 1 is a diagram showing an overall configuration of a medical imaging apparatus including a medical image processing apparatus of the invention.

Hereinafter, medical image processing apparatuses according to embodiments of the invention will be described with reference to the drawings. In all the drawings referred to in the present specification, the same elements are denoted by the same reference numerals, and a repetitive description thereof will be omitted. In the following embodiments, a case where a medical image is an ultrasonic image will be described as an example, but a medical image to be processed by the medical image processing apparatus of the invention can be applied without being limited to the ultrasonic image.

Firstly, an embodiment of a medical imaging apparatus common in each embodiment will be described.

Figure 2:
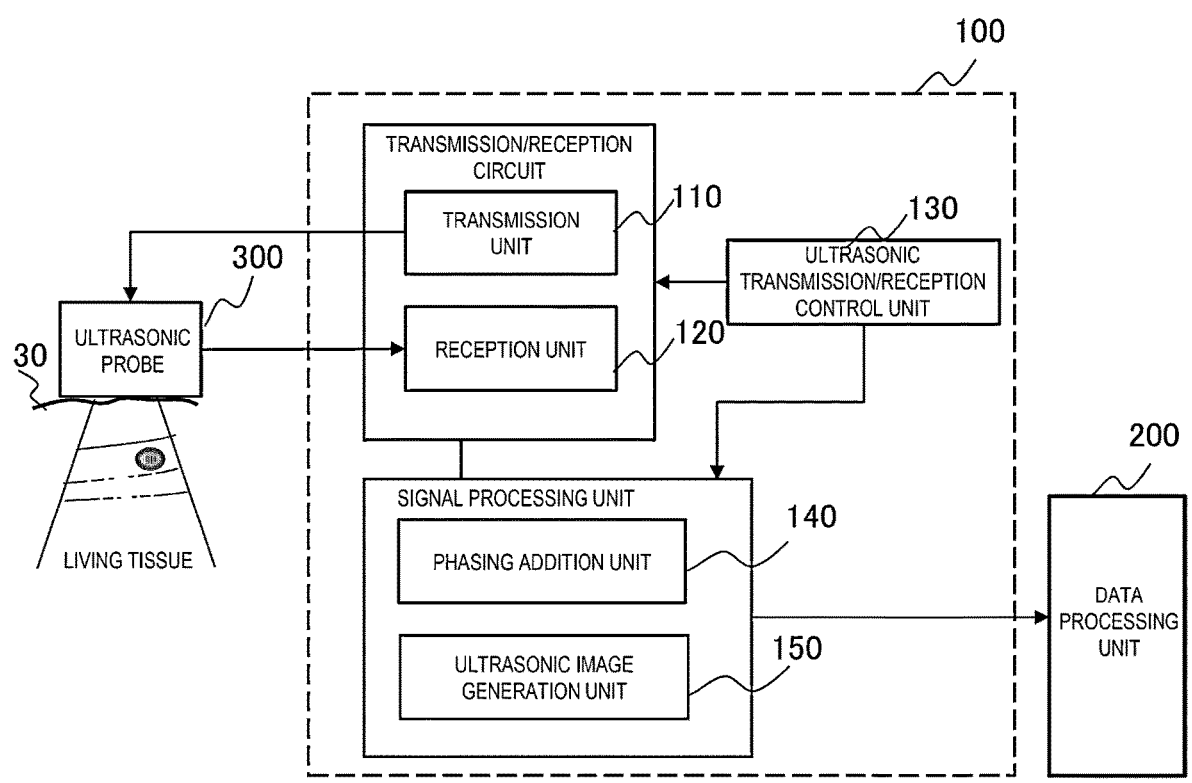
FIG. 2 is a diagram showing an overall configuration in a case where an imaging unit is an ultrasonic imaging apparatus.

As shown in FIG. 1, the medical imaging apparatus according to the present embodiment roughly includes an imaging unit 100 and a data processing unit 200. The imaging unit 100 according to the present embodiment is an imaging device that visualizes an internal structure of a subject by using ultrasonic waves, and includes, as shown in FIG. 2, a transmission unit 110 to which an ultrasonic probe 300 is connected and that transmits an ultrasonic signal to a subject 30 via the ultrasonic probe 300, a reception unit 120 that receives a reflected echo signal from the subject 30 received by the ultrasonic probe 300, an ultrasonic transmission/reception control unit 130 that controls operations of the transmission unit 110 and the reception unit 120, a phasing addition unit 140 that performs phasing of the ultrasonic signal, an ultrasonic image generation unit 150, and the like. The data processing unit 200 includes an image processing unit 210, an input unit 220, an output unit 230, and a storage device 240.

In the imaging unit 100, for example, the transmission unit 110 controlled by the ultrasonic transmission/reception control unit 130 repeatedly transmits ultrasonic waves to the subject 30 via the ultrasonic probe 300, and the reception unit 120 receives time-series reflected echo signals generated from the subject 30. The reflected echo signal is converted into time-series RF signal frame data by the phasing addition unit 140, converted into an ultrasonic image by the ultrasonic image generation unit 150 incorporating an analog-to-digital (A/D) converter (not shown), and transmitted to the image processing unit 210 of the data processing unit 200.

The image processing unit 210 analyzes the transmitted ultrasonic image, and performs processes such as detection of a lesion and a validity determination of a detection result. The input unit 220 includes an input device such as a keyboard, a mouse, a touch panel, or a button, and receives an operation from a user. The output unit 230 includes an output device such as a display (display unit), a printer, or a speaker, and outputs the ultrasonic image generated by the image processing unit 210 and a detection result of the lesion. The storage device 240 includes a magnetic disk, an optical disk, and the like, and stores data and a desired program.

Figure 3:
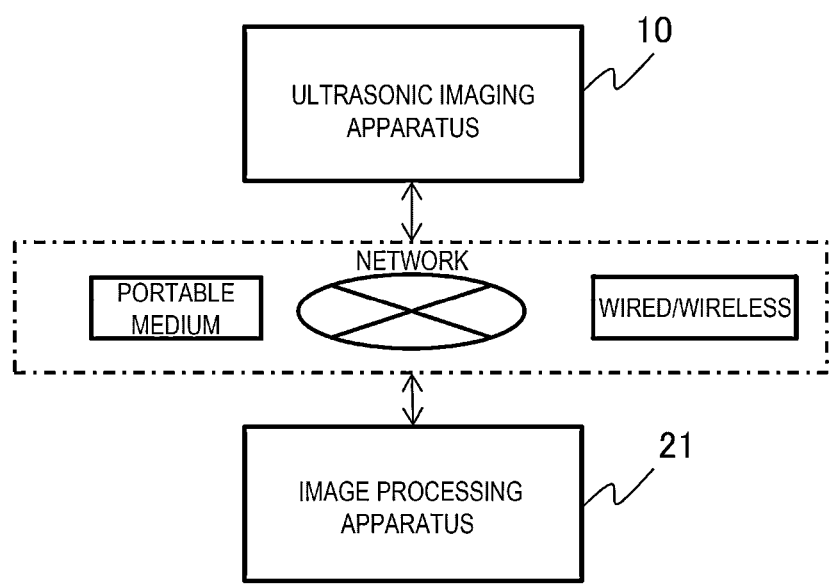

All components in the data processing unit 200 or a part of components including the image processing unit 210 can be constructed on a computer or a workstation including a CPU, a GPU, and a memory, and a function thereof is implemented by the CPU or the GPU reading preprogrammed software. A part of functions of the image processing unit 210 can be implemented by hardware such as an ASIC or an FPGA. Such a data processing unit 200 may be provided on an ultrasonic imaging apparatus same as the imaging unit 100, or may be configured as a server or the like on a network in addition to an external device connected to the imaging unit 100. When the data processing unit 200 is configured as an external device, a server on a network, or the like, as shown in FIG. 3, an ultrasonic image output by an ultrasonic imaging apparatus 10 including the imaging unit 100 is transmitted to an image processing apparatus 21 by wired or wireless communication, and a result thereof is transmitted again, if necessary, to an inside of the ultrasonic imaging apparatus 10.

Figure 4:
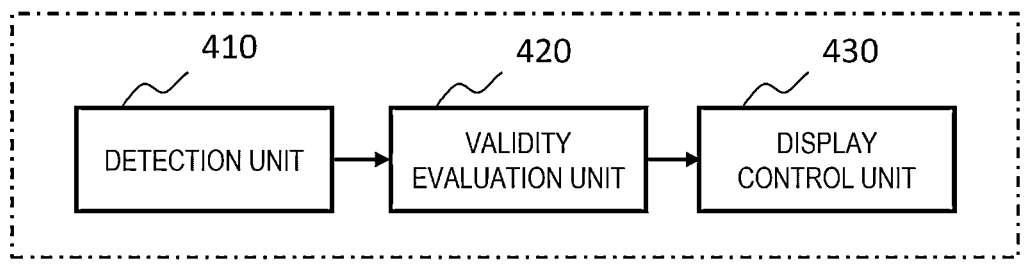
FIG. 4 is a diagram showing a configuration example of an image processing apparatus common in each embodiment.

A configuration example of the image processing unit 210 (image processing apparatus 21) is shown in FIG. 4. As shown in FIG. 4, the image processing unit 210 includes a detection unit 410 that detects a lesion candidate region with respect to an ultrasonic image obtained from the imaging unit 100, a validity evaluation unit 420 that evaluates validity of the lesion candidate region detected by the detection unit 410 (validity of a detection result), and a display control unit 430 that generates display content of the lesion candidate region by using the evaluation result of the validity evaluation unit and displays the display content on a display of the output unit 230.

An outline of processing performed by the image processing unit 210 according to the present embodiment will be described with reference to the flow of FIG. 5. First, when the imaging unit 100 receives an ultrasonic image (S51), the detection unit 410 detects a lesion candidate region from the ultrasonic image (S52). A detection method is not limited, but a detection method using machine learning is adopted. As a machine learning method, for example, methods such as a convolutional neural network (CNN), a support vector machine (SVM), and an adaboost are known, and one or more of these existing learning methods can be used in combination. For example, when the CNN is adopted, the detection unit 410 extracts features by repeating convolution processing and pooling processing on the input ultrasonic image, and calculates a position of the lesion candidate region as an output value. By adopting the CNN, a probability score of the lesion candidate region can also be output as a certainty factor. The lesion candidate region is output as a region having a predetermined shape surrounding the lesion, for example, a rectangular region. Position information may be any information as long as the lesion candidate region can be specified, and if the lesion candidate region is rectangular, the position information is acquired as, for example, a coordinate value of each vertex, a set of center coordinates, a width, and a height of the region, or the like.

Next, the validity evaluation unit 420 evaluates validity of the lesion candidate region detected by the detection unit 410 (S53). Therefore, based on structural features of the lesion and the tissue in which the lesion generates, the validity evaluation unit 420 first extracts tissue around the lesion candidate region in the medical image as normal tissue, compares features of an image of the extracted normal tissue region with features of the image of the detected lesion candidate region, and determines whether the detection result is valid based on a difference therebetween. This difference is an index indicating a change in a feature amount from the normal tissue to the lesion tissue, and is hereinafter referred to as a lesion-normal tissue variation feature amount or simply a variation feature amount. When the variation feature amount is large, the validity evaluation unit 420 determines that the validity is high, and when the variation feature amount is small, the validity evaluation unit 420 determines that the validity is low. The validity may be evaluated qualitatively, such as "high" or "low", or may be evaluated quantitatively by using a numerical value of the variation feature amount. In addition, in the validity determination, when the certainty factor is output together with the lesion candidate region from the detection unit 410, the certainty factor may also be used for the validity determination.

When the display control unit 430 receives the result of the validity evaluation unit 420, the display control unit 430 generates an image to be displayed on the display (S54). In addition, the result of the validity evaluation unit 420 is used for, if necessary, correction or update of the certainty factor, which is the output of the detection unit 410 (S55).

The outline of the processing performed by the image processing unit 210 has been described above, but a specific embodiment of processing performed by the validity evaluation unit 420 for a breast ultrasonic image will be described below.

First Embodiment

In the present embodiment, only a region located in a horizontal direction with respect to a lesion candidate region is extracted as a normal tissue region by using a structural feature that a malignant disease of a breast such as breast cancer often generates in layered mammary gland tissue, and lesion and normal tissue are adjacent to each other in the horizontal direction, and validity of the detected lesion candidate region is evaluated.

Figure 6:
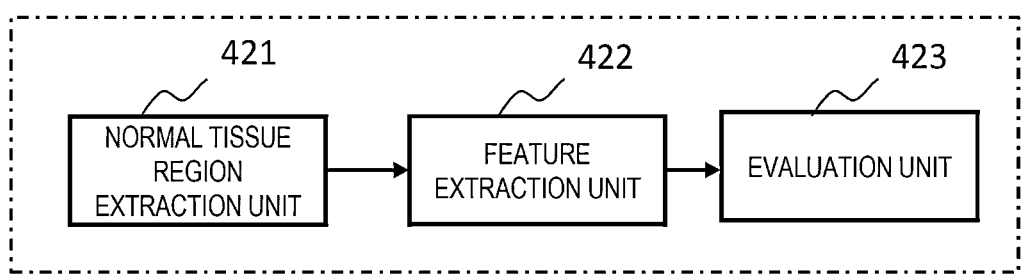
FIG. 6 is a diagram showing a configuration example of a validity evaluation unit according to a first embodiment.

FIG. 6 is a diagram showing an example of a configuration of the validity evaluation unit 420 according to the present embodiment. As shown in FIG. 6, the validity evaluation unit 420 includes a normal tissue region extraction unit 421 that extracts a normal tissue region for comparing with a lesion candidate region from an ultrasonic image, a feature extraction unit 422 that calculates a variation feature amount indicating a difference between features of images of the lesion candidate region and the normal tissue region, and an evaluation unit 423 that evaluates whether the lesion candidate region is valid as a lesion by using the calculated variation feature amount.

As shown in FIG. 7, in the validity evaluation unit 420 according to the present embodiment, in processing step S71, the normal tissue region extraction unit 421 extracts regions on both sides in the horizontal direction with respect to the lesion candidate region detected by the detection unit 410 as the normal tissue regions. Next, the feature extraction unit 422 calculates a difference between adjacent frames of the lesion candidate region and the normal tissue region in processing step S72, and further extracts a variation feature amount based on the calculated difference between the lesion candidate region and the normal tissue region in processing step S73. Finally, in processing step S74, the evaluation unit 423 evaluates the validity of the lesion candidate region based on the calculated variation feature amount. The result of the validity evaluation unit 420 is passed to the display control unit 430, and a display image to be displayed on the display is generated. Hereinafter, specific content of each processing will be described with reference to FIGS. 8A to 10. In these drawings, the same elements are denoted by the same reference numerals, and repetitive descriptions thereof will be omitted.

[Normal Tissue Region Extraction: S71]

Figure 8A:
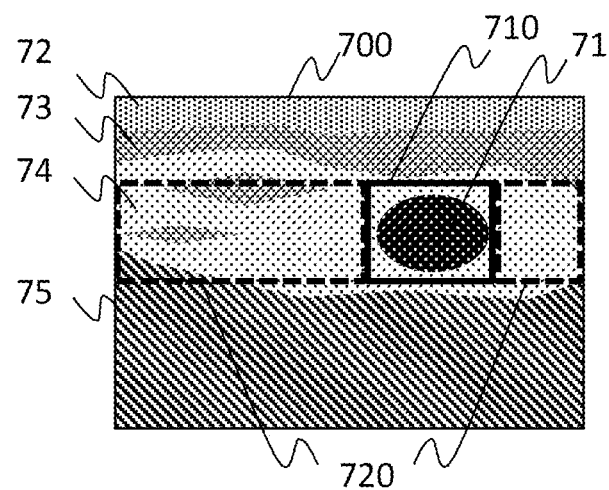
FIGS. 8A and 8B are diagrams illustrating processing of extracting a lesion candidate region and a normal tissue region and time-series difference processing for each region according to the first embodiment.

FIG. 8A shows an example of processing of extracting a lesion candidate region 710 and normal tissue regions 720 from a breast ultrasonic image 700 in the processing step S71. As shown in FIG. 8A, the breast ultrasonic image 700 includes, for example, skin 72, fat 73, a mammary gland 74, a pectoralis major muscle 75, a lesion 71, and the like, and shows a layered structure. The lesion 71 typically exists in the mammary gland 74. Therefore, with respect to the breast ultrasonic image 700, regions extended in the horizontal direction with respect to the lesion candidate region 710 detected by the detection unit 410 are extracted as the normal tissue regions 720. A width in the horizontal direction may be an entire width of the image in the horizontal direction, or may be a predetermined width corresponding to a width of the lesion candidate region 710.

[Feature Extraction: S72]

Figure 8B:
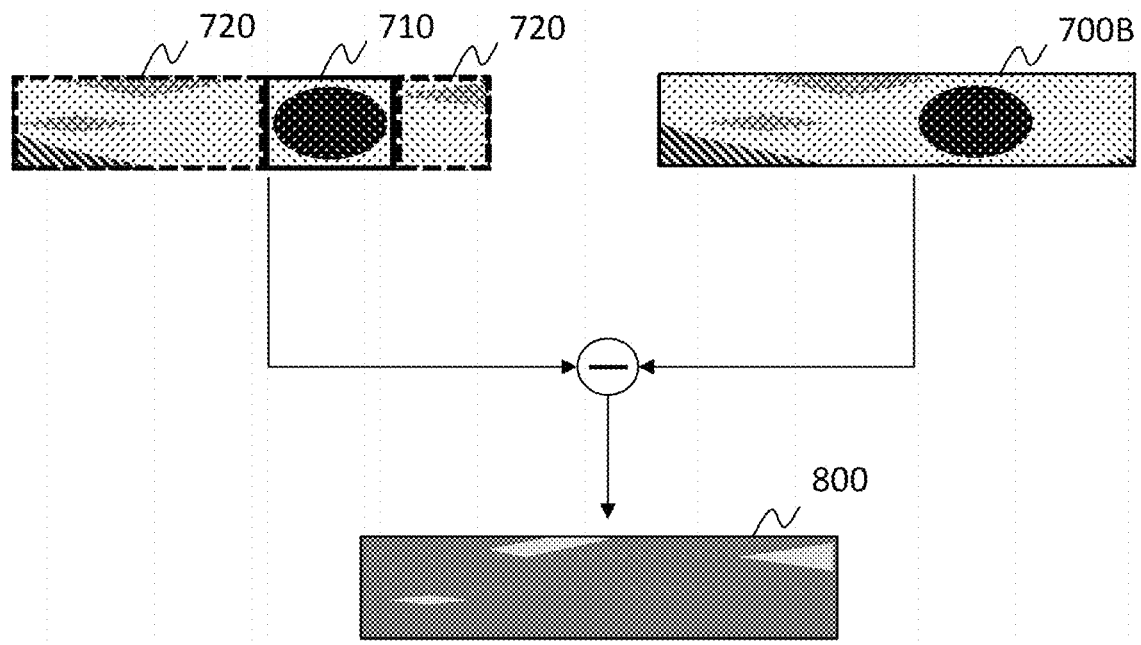

The processing step S72 is processing performed by the feature extraction unit 422 to emphasize a difference in the features of the images between the lesion tissue and the normal tissue, and as shown in FIG. 8B, a difference 800 between the lesion candidate region 710 and the normal tissue region 720 and regions at same positions of an ultrasonic image 700B one frame before is calculated. When the difference between the frames is taken, a luminance value is substantially zero, but in horizontally layered tissue such as the mammary gland tissue, a change between the frames appears as an image elongated in the horizontal direction. On the other hand, since lesion tissue such as a tumor has no layered feature, such an elongated image does not appear.

[Variation Feature Amount Calculation: S73]

Figure 9:
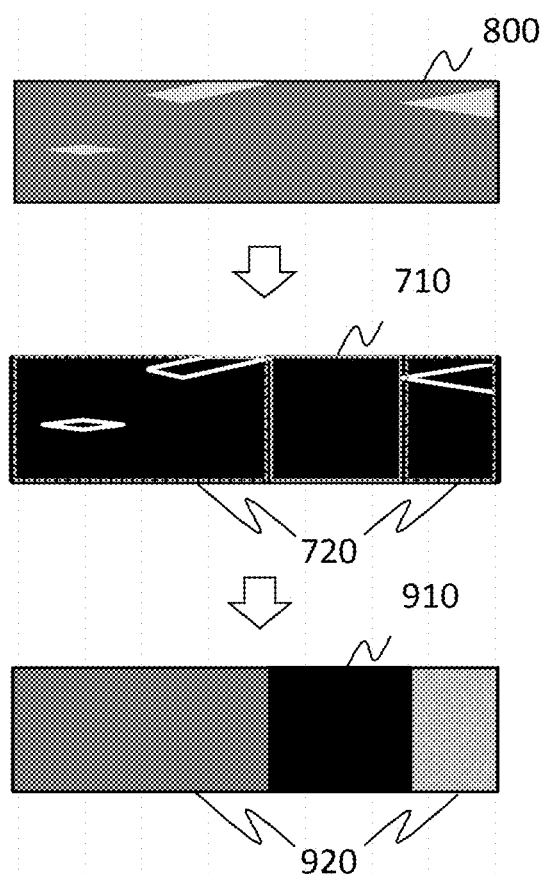
FIG. 9 is a diagram illustrating processing of calculating a lesion-normal tissue variation feature amount according to the first embodiment.

In this processing step S73, a variation feature amount of lesion-normal tissue is calculated by using a difference image. FIG. 9 shows an example of the processing. As a feature amount of an image used for calculating the variation feature amount, one or more of a luminance distribution, an edge, a texture feature, a frequency feature, and the like of each region can be used in combination, but here, the variation feature amount is calculated by using the edge and the luminance. As shown in FIG. 8B, in the difference 800, the edge mainly appears as the elongated image in the mammary gland region (normal tissue region). In order to emphasize such luminance variation of the mammary gland in the horizontal direction, the feature extraction unit 422 extracts edges in a vertical direction with respect to the difference 800. In the edge extraction, any one or a plurality of a primary differential filter, a brewitt filter, a sobel filter, a secondary differential filter, and a laplacian filter can be used in combination. In the present embodiment, the sobel filter is used.

Next, the feature extraction unit 422 calculates an average of luminance of the lesion candidate region 710 after the edge extraction, and sets the average as a lesion feature amount 910. When the average of the luminance is calculated, the luminance of the entire lesion candidate region may be used, but a calculation range may be limited to a center portion of the lesion candidate region 710 in which the lesion exists. As a result, it is possible to more stably extract the features inside the lesion. Next, an average of luminance 920 of the normal tissue region 720 after the edge extraction is calculated. In the shown example, since there are normal tissue regions on both sides of the lesion candidate region 710 in the horizontal direction, a left normal tissue feature amount 920-L and a right normal tissue feature amount 920-R are calculated for each of left and right sides. Finally, a difference between the lesion feature amount 910 and the left normal tissue feature amount 920-L and a difference between the lesion feature amount 910 and the right normal tissue feature amount 920-R are respectively calculated, and absolute values thereof are averaged to obtain the lesion-normal tissue variation feature amount.

[Validity Evaluation: S74]

The evaluation unit 423 evaluates the validity by using the variation feature amount calculated in processing step S73. In an evaluation method, only the variation feature amount may be used to determine that the validity is higher as the variation feature amount is larger and the validity is lower as the variation feature amount is smaller, but when the detection unit 410 (for example, the CNN) outputs the certainty factor together with the lesion candidate region, it is also possible to evaluate the certainty factor together with the variation feature amount.

Figure 10:
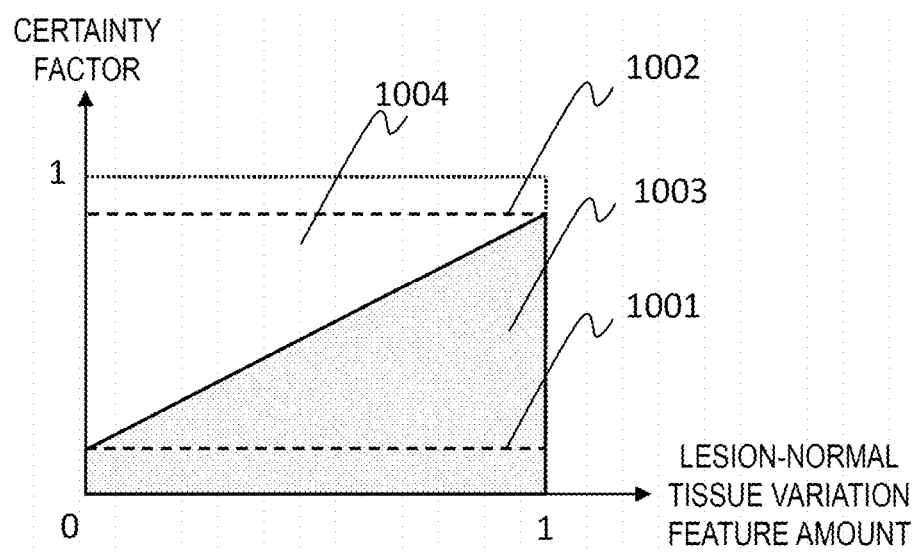
FIG. 10 is a diagram illustrating an example of a method of evaluating validity of the lesion candidate region according to the first embodiment.

FIG. 10 shows, as an example, a case where the validity is evaluated by using the variation feature amount and the certainty factor output by the detection unit 410. In a graph shown in FIG. 10, a horizontal axis represents the variation feature amount, and a vertical axis represents the certainty factor, which are represented in any units. In this example, an upper limit threshold value 1002 and a lower limit threshold value 1001 are set for the certainty factor, and between the lower limit threshold value and the upper limit threshold value, a region is divided by a line segment in which the certainty factor and the variation feature amount have a direct proportion relationship, when the certainty factor and the variation feature amount are distributed in an upper region 1004, it is evaluated that the validity is high, and when the certainty factor and the variation feature amount are distributed in a lower region (gray region) 1003, it is evaluated that the validity is low. In general, when the variation feature amount is high and the certainty factor is low, there is a high possibility that a region detected as a lesion candidate region is not a lesion such as a shadow, and that a region having different appearance from left and right is erroneously detected (false positive). In this evaluation method, such a possibility is eliminated by setting the lower limit threshold value 1001 in a range in a certainty factor direction. The upper limit threshold value 1002 and the lower limit threshold value 1001 are set to values of 0 to 1.

Figure 5:
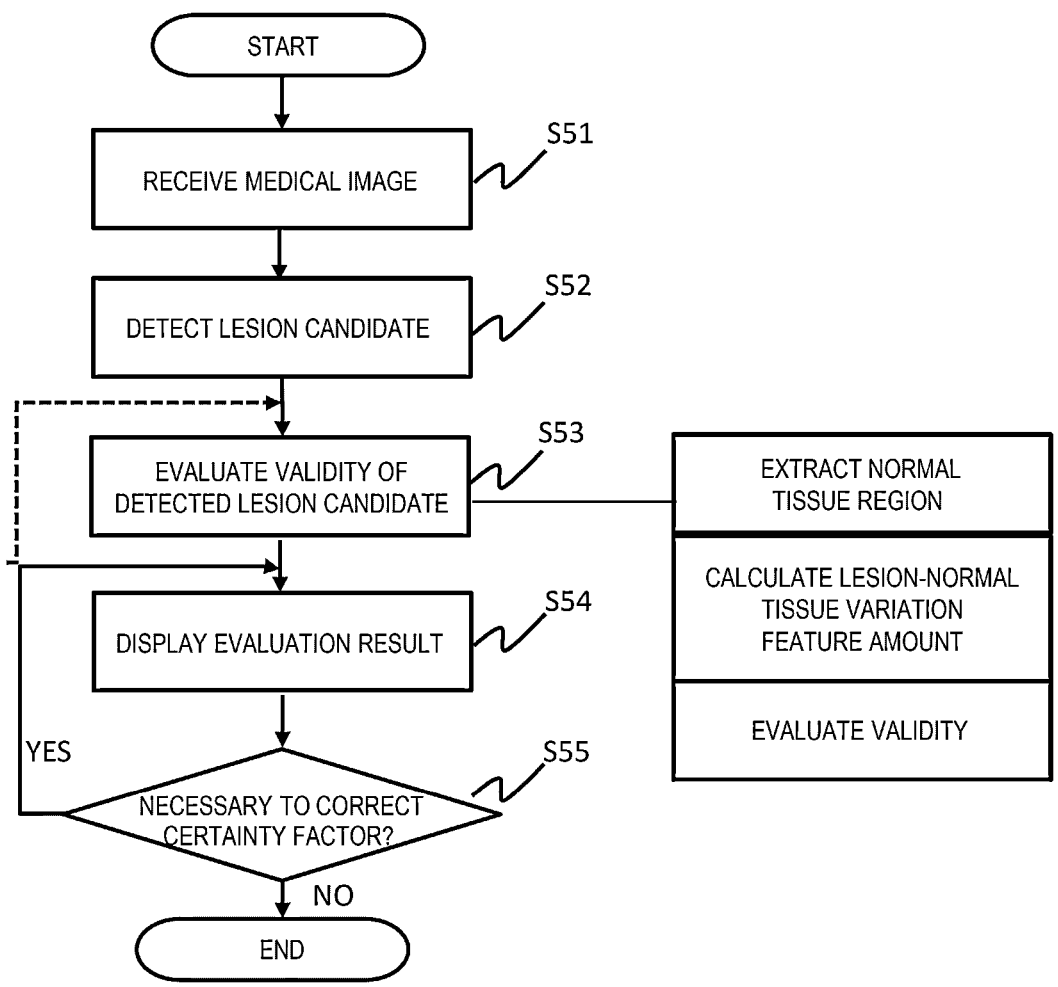
FIG. 5 is a diagram showing an outline of processing of the medical image processing apparatus.

At this time, when it is evaluated that the validity is low (the variation feature amount is small), the certainty factor may be corrected (FIG. 5: S55). For example, when the certainty factor is 80%, a value obtained by multiplying the value (80%) of the certainty factor displayed as the detection result of the detection unit 410 by a coefficient a proportional to the variation feature amount may be displayed as the certainty factor.

Finally, the evaluation result and the certainty factor are output to the output unit 230 (display) and presented to the user (FIG. 5: S54). A method of presenting to the user is not particularly limited, but specific examples of the display are shown in FIGS. 11 and 12.

Figure 11:
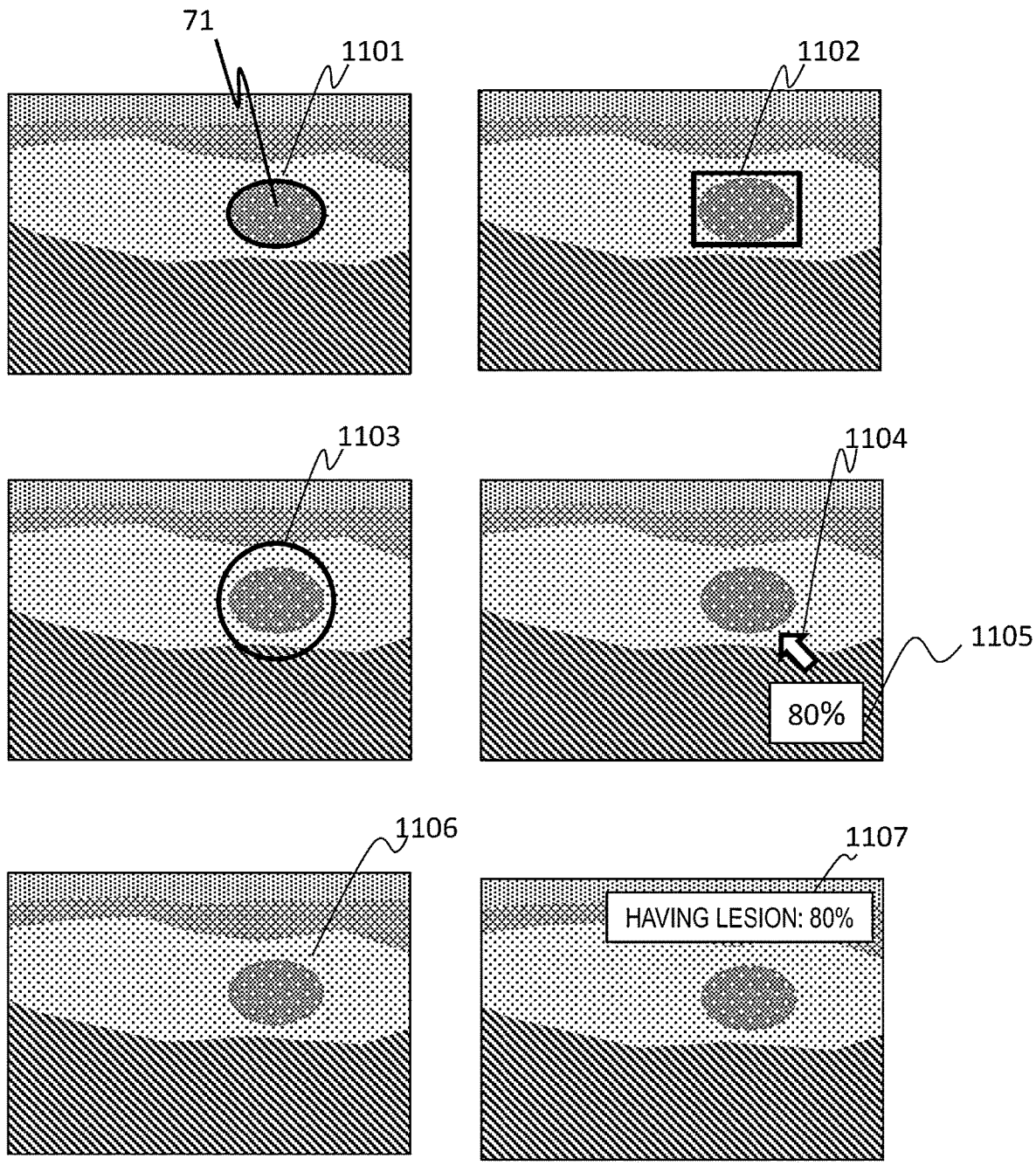
FIG. 11 is a diagram showing a display example of a display unit according to the first embodiment.

FIG. 11 is a diagram showing an example of the display content of the detection result generated by the display control unit 430. The display control unit 430 determines content to be displayed to the user based on the evaluation result of the evaluation unit 423. When the evaluation result is high, a marker indicating a presence of the lesion candidate region is presented, and when the evaluation result is low, the marker is not presented. As the marker, a shape or a contour shape 1101 superimposed on the lesion 71, a rectangle 1102 surrounding the lesion 71, a circle or an ellipse 1103, an arrow 1104 indicating the lesion, or the like may be used. In addition, the certainty factor may be displayed in a vicinity of the marker as a character string 1105. In addition, a marker 1106 in which an opacity (%) of the marker is replaced with a percentage of the certainty factor may be displayed. Instead of displaying the marker indicating a position, a character string 1107 indicating that the lesion candidate region 71 is detected from the image may be displayed.

Figure 12:
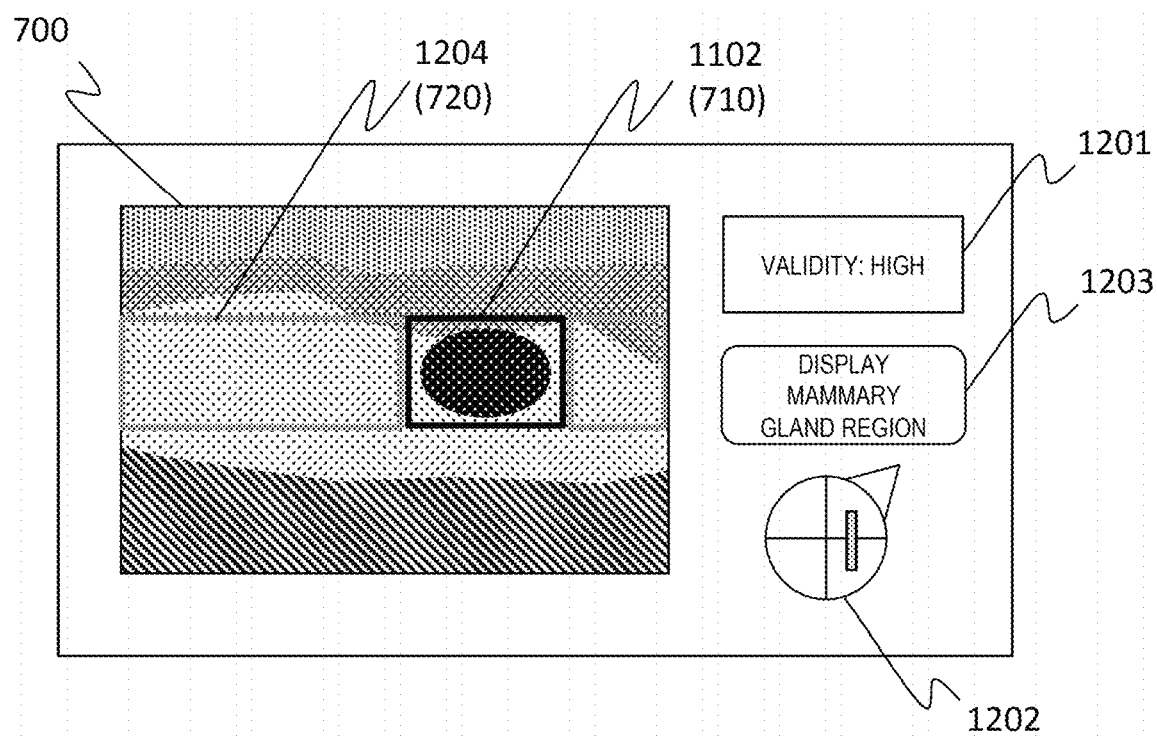
FIG. 12 is a diagram showing an example of a display screen according to the first embodiment.

FIG. 12 is a diagram showing an example of a display screen of the validity evaluation result generated by the display control unit 430, and in this example, information related to the validity evaluation is displayed side by side with the display screen on which the ultrasonic image 700 is displayed. In the ultrasonic image 700, the marker 1102 or the character string indicating the presence of the lesion candidate region 710 is displayed. A validity evaluation result 1201 is displayed in a qualitative expression such as "validity: high", and position information 1202 is displayed when the position information is acquired. In the shown example, the position information 1202 indicates a shape of a breast in a circular shape, displays a figure (triangle) indicating one of the right and left sides, and indicates a position (or the positions of the normal tissue region and the lesion region, or a position detected as the lesion candidate region) of the region projected as the ultrasonic image 700 in a square block. Therefore, it is possible to confirm where a lesion is detected in the left or right breast. In addition to the qualitative expression, the evaluation result 1201 may be expressed, as shown in FIG. 10, by a numerical value obtained by combining numerical values of the variation feature amount and the certainty factor, for example, a numerical value that is weighted and added, when the validity is evaluated by combining the variation feature amount and the certainty factor.

In addition, a mammary gland region display button 1203 for executing the display of the normal tissue region 720 used for the validity evaluation may be displayed. When the mammary gland region display button 1203 is pressed, a marker 1204 indicating a presence of the normal tissue region 720 is displayed. As the marker 1204 indicating the presence of the normal tissue region 720, markers same as the markers 1101 to 1106 indicating the presence of the lesion candidate region 710 as shown in FIG. 11 can be used.

By displaying such a marker, the user can confirm validity of tissue regarded as the normal tissue and reliability of the validity evaluation result based on the validity.

As described above, according to the present embodiment, with respect to the region in which it is detected that the lesion exists, the region in the horizontal direction is extracted and regarded as the normal tissue region, and the variation feature amount is calculated based on a difference between features of the two regions, so that it is possible to appropriately determine validity of the lesion detection in a breast formed of layered tissue without performing a time-consuming analysis such as an anatomical analysis. As a result, erroneous detection can be reduced in real time, and efficiency of medical examination performed by an operator can be improved.

Modification of First Embodiment

In the first embodiment, the left and right regions of the lesion tissue region in the horizontal direction are set as the normal tissue regions, and the average value of the luminance of the entire region is calculated, but in order not to impair a luminance feature in the horizontal direction, the normal tissue region may be divided in the vertical direction, and the average value of the luminance may be calculated for each of the divided regions.

Figure 13:
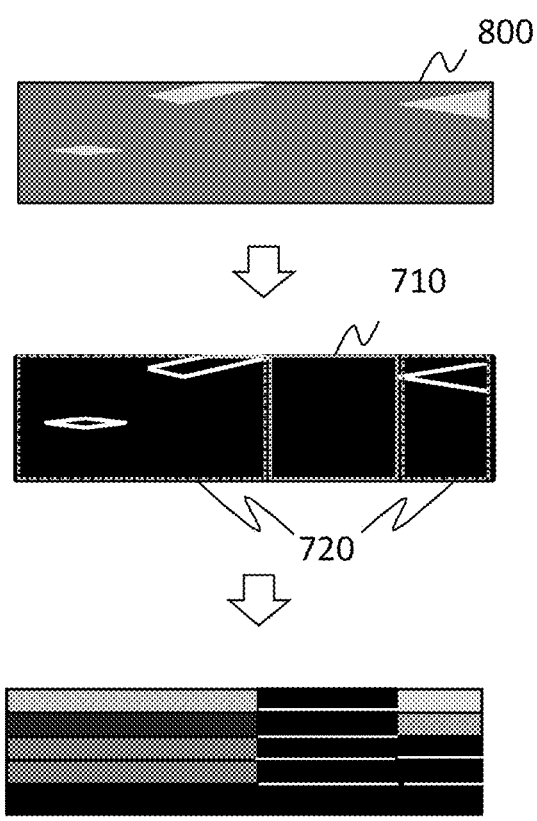
FIG. 13 is a diagram illustrating a modification of the first embodiment.

Also in this case, as shown in FIG. 9, the edge extraction after obtaining the difference between the images for each of the lesion candidate region 710 and the normal tissue region 720 between the frames is the same as in the first embodiment, but as shown in FIG. 13, the lesion candidate region 710 and the normal tissue region 720 are divided into small regions 730, and an average value of luminance values in an edge extraction image is obtained for each small region. Differences (absolute values) between the average value obtained in each small region and the average value of the luminance value of the lesion candidate region are calculated, and the variation feature amount is calculated based on an average value of the absolute values of the differences in the small regions. Alternatively, a set or a vector of the values (average values of luminance values) of the respective small regions of the normal tissue region 720 and the lesion candidate region 710 may be obtained, a similarity between the regions may be calculated, and the variation feature amount may be obtained based on the similarity. In this case, the higher degree of the similarity is, the smaller the variation feature amount is, and the lower degree of the similarity is, the larger the variation feature amount is. When the similarity is calculated based on the vector, a cosine similarity, a Pearson's correlation coefficient, a Spearman's rank correlation coefficient, and the like can be used. When the similarity is calculated based on the set, a Jaccard coefficient, a dice coefficient, a Simpson coefficient, and the like can be used in addition to the above similarity.

In the first embodiment, the edge of each region is used as the feature amount, but one or more of a luminance distribution, the edge, a texture feature, a frequency feature, and the like may be used in combination as the feature amount. The texture feature refers to a feature amount representing texture of a certain region of an image, and is represented by a statistical amount representing non-uniformity by a statistical-based method.

Further, in the present embodiment, as a structural feature taken into consideration when a normal tissue region is extracted, a feature that lesion tissue and normal tissue are adjacent to each other in the horizontal direction, such as layered mammary gland tissue, is used, but when the normal tissue is organ tissue surrounding a lesion, such as a lesion generating in an organ, various changes can be made by extracting a donut-shaped region so as to surround a circular lesion candidate region and setting the donut-shaped region as a normal tissue region, for example.

Second Embodiment

Figure 14:
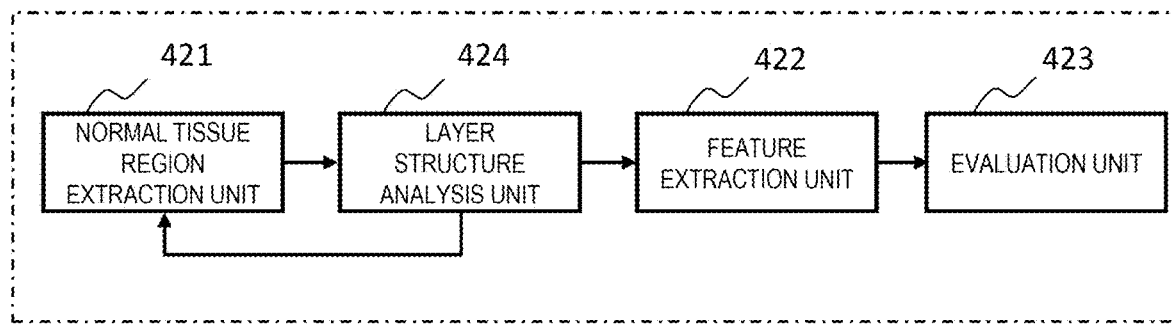
FIG. 14 is a diagram showing a configuration example of a validity evaluation unit according to a second embodiment.

Also in the present embodiment, the normal tissue is extracted by basically using a fact that a tissue structure is layered, but the normal tissue region is extracted more accurately by taking inclination of the layer structure of the ultrasonic image into consideration, and erroneous detection can be reduced with high accuracy. Also in the present embodiment, an overall configuration of the apparatus is the same as the configuration shown in FIGS. 1 and 4. FIG. 14 is a diagram showing a configuration example of the validity evaluation unit 420 according to the present embodiment. In FIG. 14, the same elements as those in FIG. 6 are denoted by the same reference numerals, and the description thereof will be omitted. The validity evaluation unit 420 of the present embodiment includes a layer structure analysis unit 424 that analyzes a layer structure based on the output of the normal tissue region extraction unit 421 and outputs a result to the normal tissue region extraction unit 421.

A flow of processing performed by the validity evaluation unit 420 is substantially the same as the processing of the first embodiment shown in FIG. 7, but is different in that in step S71 of extracting the normal tissue region, the layer structure analysis unit 424 analyzes a region extracted by the normal tissue region extraction unit 421 and corrects the normal tissue region. Hereinafter, processing performed by the layer structure analysis unit 424 will be described.

The layer structure analysis unit 424 first performs the edge detection on the normal tissue region 720, and then calculates inclination. In the edge detection, as described with reference to FIG. 9 in the first embodiment, an edge is extracted by using the sobel filter with respect to a difference between frames. Next, inclination of the extracted edge is calculated. A method of calculating the inclination is not limited, but a case of using two-dimensional fast Fourier transform (2D-FFT) will be described as an example.

Figure 15:
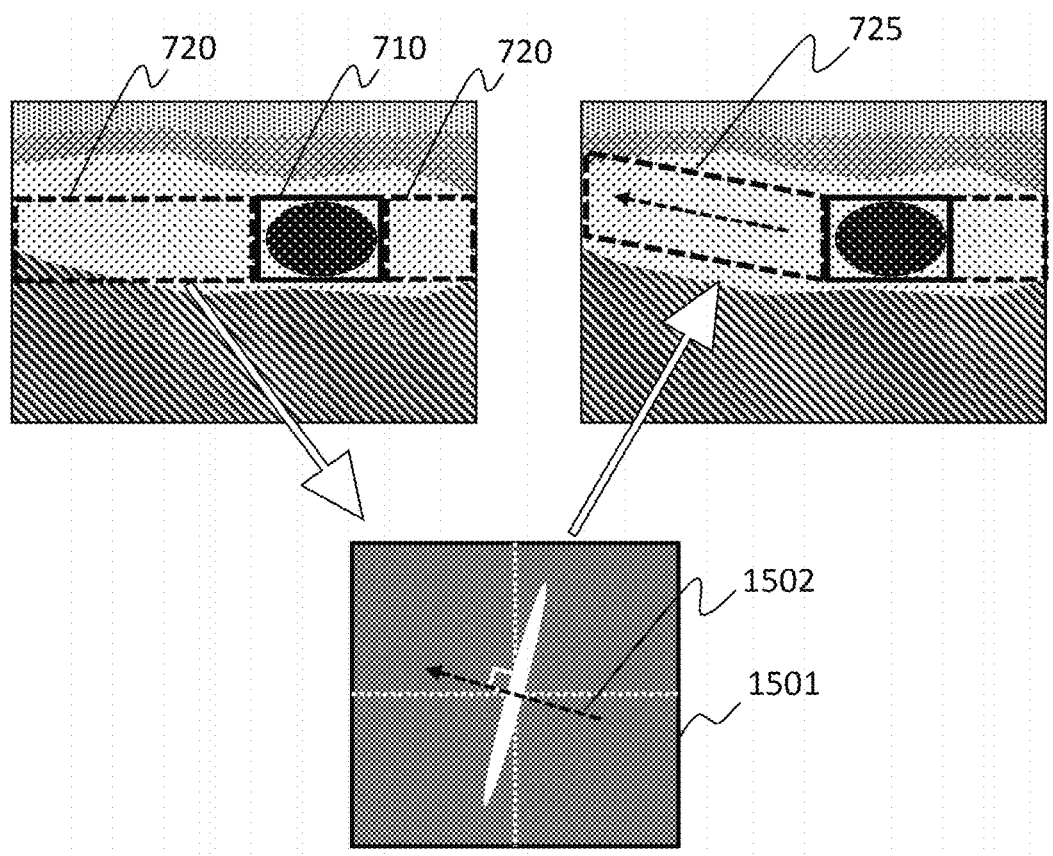
FIG. 15 is a diagram illustrating extraction of a normal tissue region and correction processing for the extraction according to the second embodiment.

The edge is subjected to 2D-FFT and is converted into data in a frequency domain. As shown in FIG. 15, the edge appears as a remarkable luminance change in an angular direction at polar coordinates ($0 \leq \theta \leq \pi$) 1501 in the frequency domain. An angle orthogonal to an angle at which a peak value of this luminance change is obtained is a direction of the edge. Therefore, inclination 1502 of the layer structure can be calculated by subtracting $\pi/2$ from the angle at which the peak value is obtained. When the normal tissue regions 720 exist on both sides of the lesion candidate region 710, the inclination is calculated for each region. The layer structure analysis unit 424 compares an absolute value of the slope 1502 with a predetermined threshold value, determines that the layer structure is inclined in the normal tissue region 720 when the absolute value is equal to or greater than a threshold value, and transmits the inclination to the normal tissue region extraction unit 421.

The normal tissue region extraction unit 421 uses the transmitted inclination to transform the normal tissue region 720 into a parallelogram in which the normal tissue regions 720 are continuous with both ends of the lesion candidate region 710, and sets the parallelogram as a new normal tissue region 725. In the calculation of the inclination, the normal tissue region 720 may be equally divided into upper and lower regions, the inclination may be similarly calculated for each of the upper and lower regions, and a trapezoid in which angles of upper and lower two sides of the normal tissue region 720 (rectangle) are updated with the inclination may be set as a new normal tissue region. Thereafter, a variation feature amount is calculated based on feature amounts of the new normal tissue region 725 and the lesion candidate region 710, and validity is evaluated in the same manner as in the first embodiment.

According to the present embodiment, since the normal tissue region is extracted along the inclination of the layer structure, the erroneous detection can be reduced with higher accuracy.

Third Embodiment

In the first and second embodiments, the region connected to the lesion region candidate in the horizontal direction is extracted as the normal tissue region, but in the present embodiment, not only the regions adjacent to the lesion candidate region in the horizontal direction but also a lower layer region is extracted, and a variation feature amount of the lower layer region is also used. Accordingly, the erroneous detection can be reduced with high accuracy. Also in the present embodiment, an overall configuration of the apparatus is the same as the configuration shown in FIGS. 1 and 4.

Figure 16:
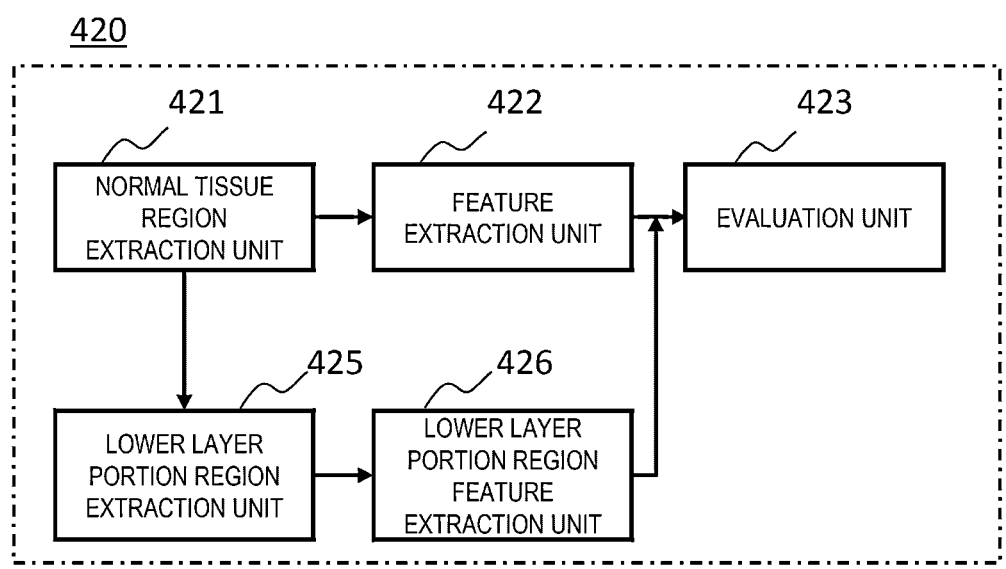
FIG. 16 is a diagram showing a configuration example of a validity evaluation unit according to a third embodiment.

FIG. 16 is a diagram showing a configuration example of the validity evaluation unit 420 according to the present embodiment. In FIG. 16, the same elements as those in FIG. are denoted by the same reference numerals, and the description thereof will be omitted. The validity evaluation unit 420 of the present embodiment includes a lower layer portion region extraction unit 425 that extracts a layer structure region adjacent below the lesion candidate region from the output of the normal tissue region extraction unit 421, and a lower layer portion region feature extraction unit 426 that calculates a lower layer portion variation feature amount based on the lower layer portion region.

Processing performed by the validity evaluation unit 420 according to the present embodiment, in addition to the processing of the first embodiment shown in FIG. 7, further includes a step of adding processing of calculating a variation feature amount (lower layer portion variation feature amount) also for lower sides of the lesion candidate region and the normal tissue region after the normal tissue region is extracted, and a step of determining the validity of the lesion candidate region detected by the detection unit 410 by using the lower layer portion variation feature amount by the evaluation unit 423 in addition to the lesion-normal tissue variation feature amount calculated by the feature extraction unit 422.

In a general ultrasonic image, a region below a lesion is compared with the surrounding tissue to observe a luminance change such as lower or higher luminance, due to echo attenuation or backscattering 1601. Therefore, by comparing luminance distributions of the lower side of the lesion and the lower side of the normal tissue, it is possible to obtain information for determining the validity of the lesion tissue detection.

Figure 17:
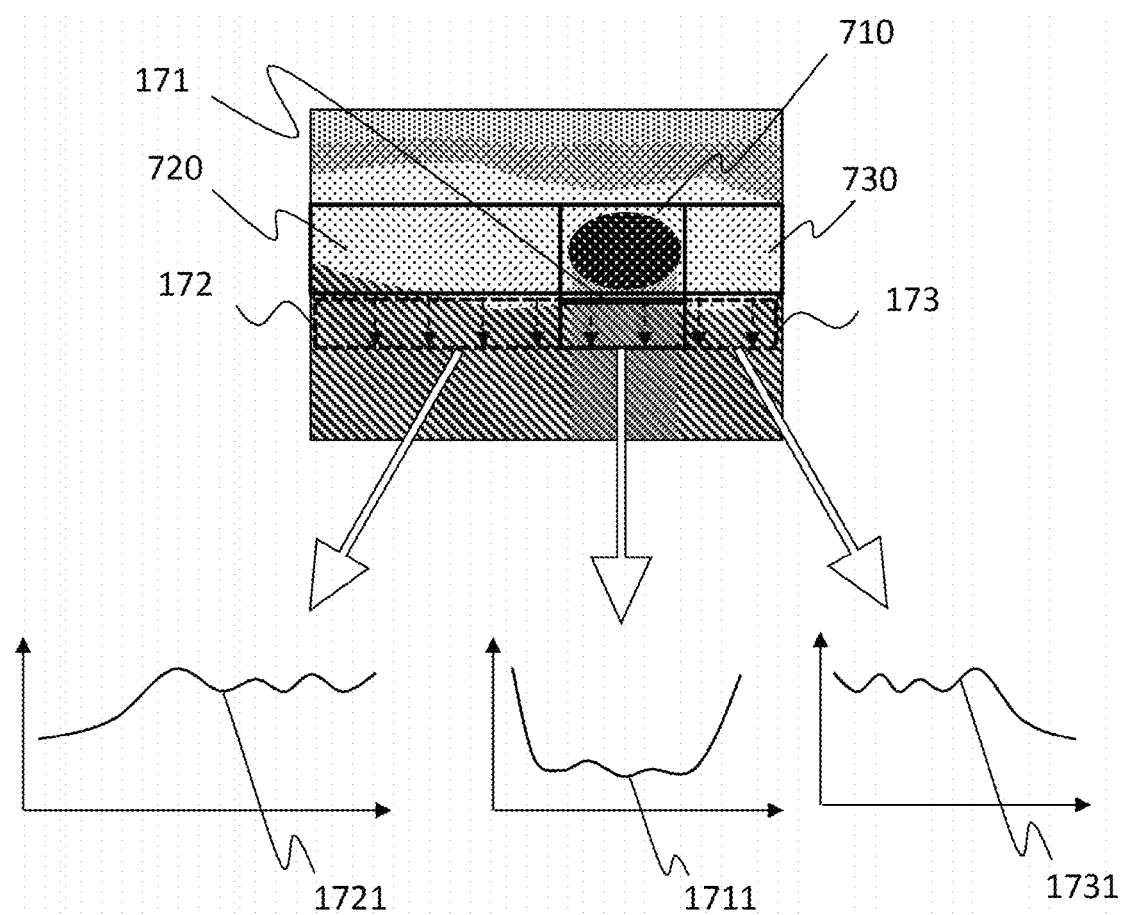
FIG. 17 is a diagram illustrating calculation of a variation feature amount of a lower layer portion region according to the third embodiment.

Specifically, first, the lower layer portion region extraction unit 425 sets, as shown in FIG. 17, lower side regions 171, 172, 173 with a same width below the lesion candidate region 710 and the normal tissue regions 720, 730, respectively. A height (depth) range of the lower side region may be the same as that of the lesion candidate region 710 and the normal tissue regions 720, 730, or may be a predetermined value. Next, the lower layer portion region feature extraction unit 426 calculates a similarity of the luminance distributions for the lower side regions 171, 172, 173 extracted by the lower layer portion region extraction unit 425.

In order to calculate the similarity of the luminance distributions, first, the lower side region 171 of the lesion candidate region 710 and the lower side regions 172, 173 of the normal tissue region 720 are respectively divided into small regions having a width of, for example, 1 pixel and a height of both regions, and luminance distributions 1721, 1711, 1731 are obtained based on an average value of luminance in each small region. Next, smoothing and normalization processing are performed on the luminance distributions 1721, 1711, 1731. For smoothing, for example, one or more of a moving average filter, a gaussian filter, a median filter, and the like may be used in combination. As a normalization processing method, for example, a normalized luminance average value i at a certain position is defined as follows using an original luminance average value i', a maximum value i_M of luminance of each region, and a minimum value i_m of luminance of each region.

$$i=(i'-i\_m)/(i\_M-i\_m)$$

After the luminance distribution is normalized in this manner, the similarity between the regions is calculated. In the calculation of the similarity, for example, a normalized luminance distribution (luminance value for each pixel) is converted into a set or a vector, and the similarity is calculated. As a method of calculating the similarity, the method exemplified in the modification of the first embodiment can be used, for example, if the similarity between the vectors is calculated, the cosine similarity, the Pearson's correlation coefficient, the Spearman's rank correlation coefficient, and the like can be used, and when the similarity between the sets is calculated, the Jaccard coefficient, the dice coefficient, the Simpson coefficient, and the like can be used in addition to the above similarity.

The lower layer portion region feature extraction unit 426 converts the similarity into the lower layer portion variation feature amount, and outputs the lower layer portion variation feature amount to the evaluation unit 423. In this conversion, the higher degree of the similarity is, the smaller the lower layer portion variation feature amount is, and the lower degree of the similarity is, the larger the lower layer portion variation feature amount is.

The evaluation unit 423 calculates plausibility of the lesion in the lesion candidate region 710 output by the detection unit 410 by using both or one of the lesion-normal tissue variation feature amount obtained from the feature extraction unit 422 and the lower layer portion variation feature amount obtained from the lower layer portion feature extraction unit 426, and evaluates the validity. Examples of a method of calculating the plausibility include processing of multiplying a simple average or a weighted average of two feature amounts by a constant. A coefficient of a weight of the weighted average, or the like may be a fixed value or may be manually adjustable. Alternatively, a small-scale converter using machine learning such as the CNN may be introduced into the evaluation unit 423, and the plausibility may be directly calculated based on each variation feature amount.

As described above, according to the present embodiment, the features of the lower side regions in addition to the normal tissue region can be used for the validity evaluation, and the erroneous detection can be reduced more accurately and stably.

Among the processing of the validity evaluation unit of the present embodiment, for the same processing as those of the first embodiment, in addition to the processing described in the first embodiment, the processing described as the modification of the first embodiment and the method of the second embodiment can be combined.

Fourth Embodiment

In the first to third embodiments, the validity evaluation unit 420 determines the validity (positive-true, positive-false) of the lesion candidate region detected by the detection unit 410, but the present embodiment is characterized in that a function of determining detection omission (negative-false) is added.

Figure 18:
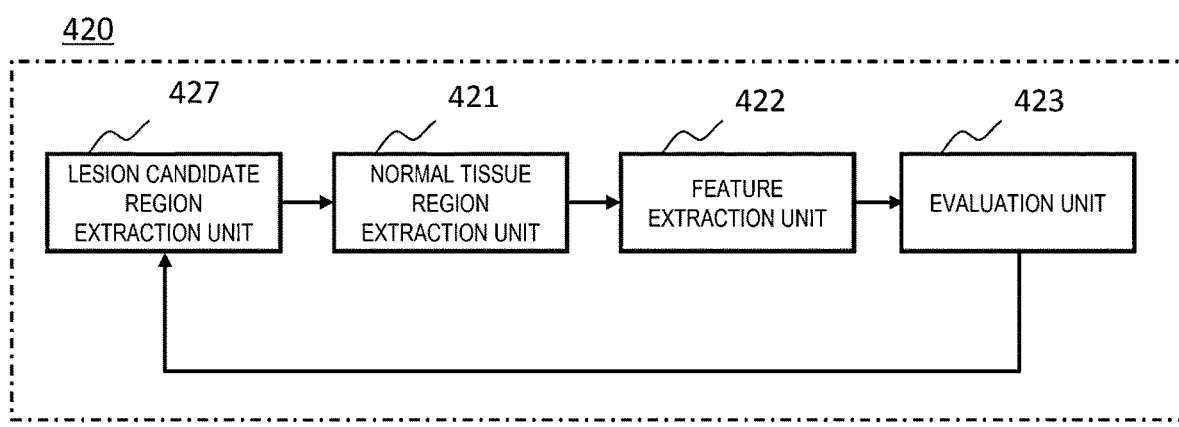
FIG. 18 is a diagram showing a configuration example of a validity evaluation unit according to a fourth embodiment.

Also in the present embodiment, an overall configuration of the image processing unit is the same as the configuration shown in FIG. 4. FIG. 18 is a diagram showing a configuration example of the validity evaluation unit 420 according to the present embodiment. In the present embodiment, a lesion candidate region extraction unit 427 that extracts a lesion candidate region is provided in front of the normal tissue region extraction unit 421.

Figure 19:
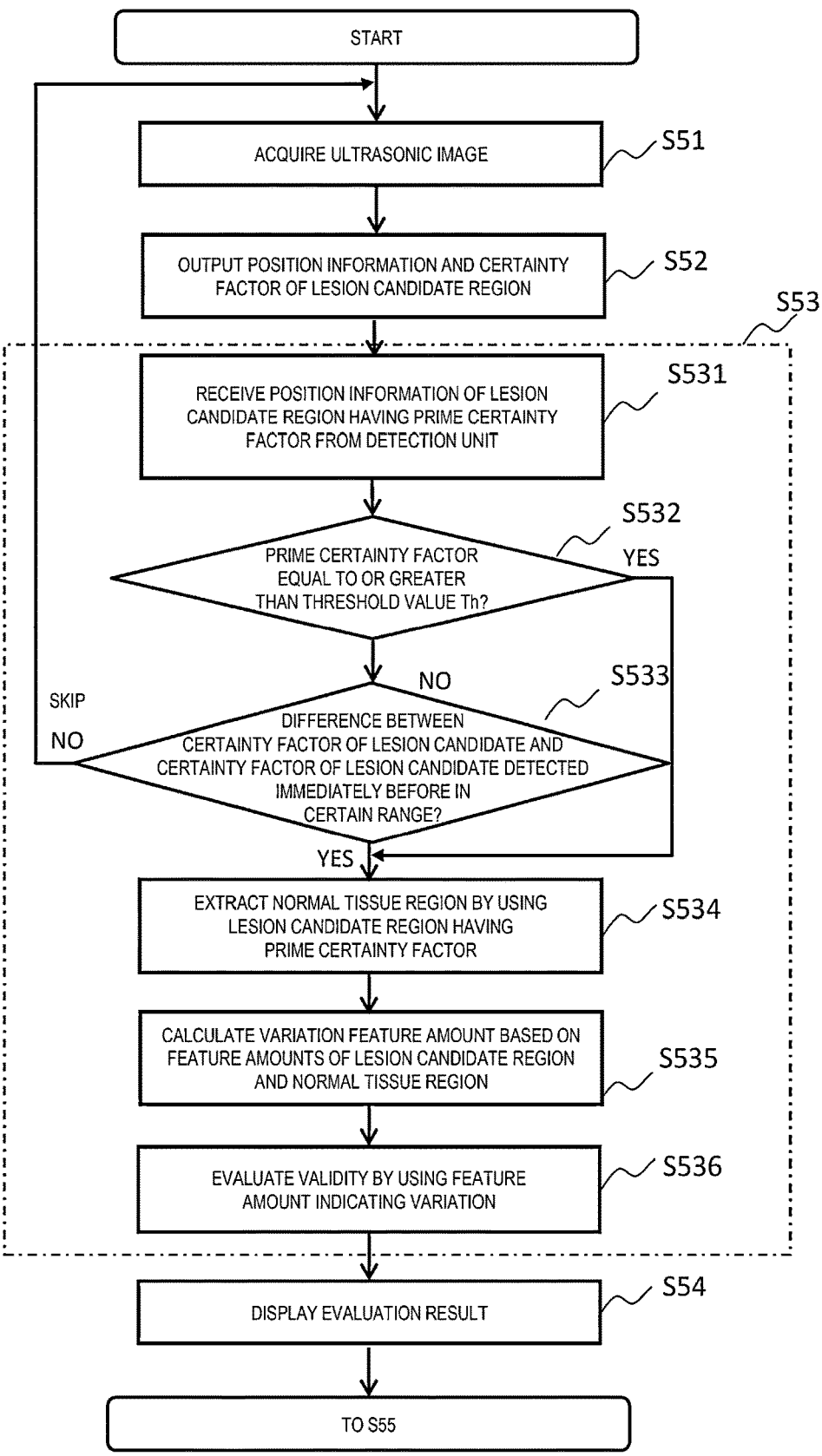
FIG. 19 is a diagram showing a flow of processing according to the fourth embodiment.

A flow of processing of the validity evaluation unit 420 of the present embodiment will be described with reference to FIG. 19. In FIG. 19, the same processing as those in FIG. 5 are denoted by the same reference numerals, and repetitive descriptions thereof will be omitted. Here, as a premise, it is assumed that the detection unit 410 holds therein a plurality of detection results, for example, data detected for each frame, data detected immediately before, and the like.

First, regardless of whether a lesion candidate is detected, the detection unit 410 outputs a certainty factor and a position of the lesion candidate region having a highest certainty factor among a plurality of detection results to the lesion candidate region extraction unit 427 (S52). The lesion candidate region extraction unit 427 receives the position and the certainty factor as prime position information and prime certainty factor (S531), determines whether the prime certainty factor is equal to or greater than a predetermined threshold value Th (S532), and when the prime certainty factor is equal to or greater than the threshold value Th, outputs the prime position information as it is to the normal tissue region extraction unit 421 as a lesion candidate region (proceeding to S534). When the prime certainty factor is less than the threshold value Th, in a case where the detection unit 410 continuously detects a certain number of lesion candidate regions up to a previous frame or in a case where there is a previous detection result, the prime certainty factor is compared with a certainty factor of a lesion candidate detected in the previous frame or a certainty factor of a lesion candidate detected immediately before (S533). When it is determined in step S533 that a difference between the certainty factor of the lesion candidate and the certainty factor of the lesion candidate detected immediately before exceeds a certain range, steps after step S534 are skipped, and the processing proceeds to acquisition of a next ultrasonic image (S51).

On the other hand, when the difference is within the certain range in step S533, the prime position information received in step S531 is output to the normal tissue region extraction unit 421 as the lesion candidate region. At this time, the prime certainty factor is also output at the same time. The normal tissue region extraction unit 421 extracts a normal tissue region by using the prime position information, and as in the first embodiment, the feature amount extraction unit 422 performs calculation of a variation feature amount and the evaluation unit 423 performs the validity determination (S534 to S536). Thereafter, the display control unit 430 determines display content to the user based on the evaluation result (S54). As described above, even when the certainty factor is low, a step of determining the difference from the certainty factor detected immediately before is added without immediately skipping the processing, thereby preventing the detection omission.

Figure 20:
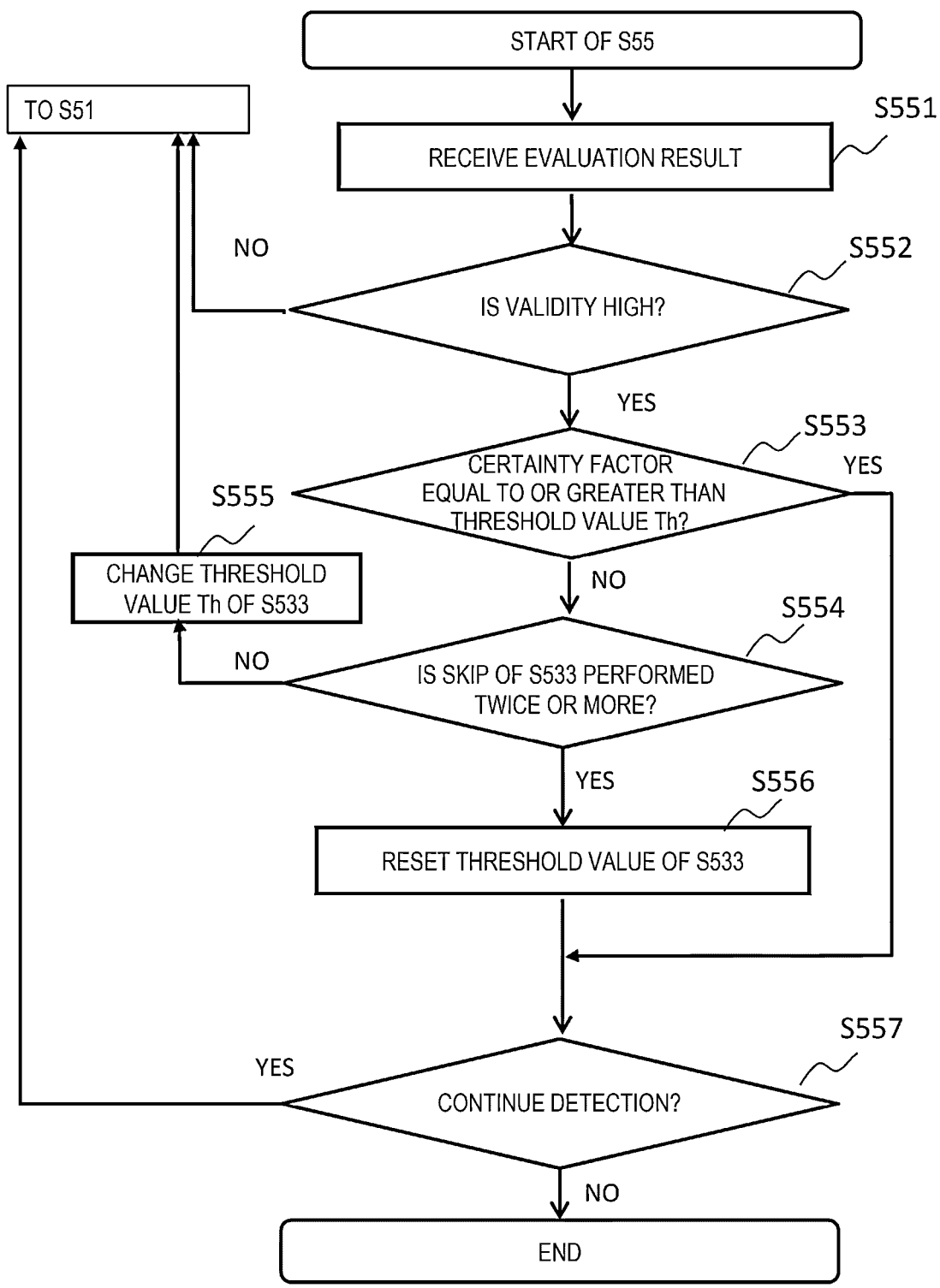
FIG. 20 is a diagram illustrating a flow of processing according to the fourth embodiment following the processing of FIG. 19.

Further, after the determination performed by the evaluation unit 423, the lesion candidate region extraction unit 427 receives a result of the evaluation unit 423 and updates the threshold value Th of the certainty factor to be used after skipping the processing (acquiring the ultrasonic image again) if necessary (S55). Details of update processing (S55) are shown in FIG. 20. That is, the evaluation result of the validity is received (S551), and when the certainty factor of the lesion candidate region evaluated as high validity is equal to or less than a predetermined threshold value (S552, S553), the threshold value Th used in the determination (S532) of skipping the processing by the lesion candidate region extraction unit 427 is updated to the same value as the certainty factor (S555). Therefore, the detection omission is prevented. However, in order to reduce the erroneous detection due to the low threshold value Th, this update is reset at the time when the skip processing is performed twice in succession in the lesion candidate region extraction unit 427 (S554), and the threshold value returns to an initial value (S556). When the validity is high and the certainty factor is larger than the predetermined threshold value in steps S552, S533, the processing ends if an examination is not continued (S556, S557).

As described above, according to the present embodiment, the detection omission can be prevented, and a stable computer-aided detection can be performed. Also in the present embodiment, the processing of the validity evaluation of steps S534 to S536 can be performed by appropriately combining the methods of the first embodiment, the modification thereof, or the second embodiment.

The embodiments of the medical image processing apparatus and the medical imaging apparatus of the invention has been described above by taking the processing of the breast ultrasonic image as an example, but the medical image processing apparatus and the medical imaging apparatus of the invention can be applied not only to an apparatus for processing an ultrasonic image but also to a medical image processing apparatus or a medical imaging apparatus such as an X-ray imaging apparatus or a CT apparatus as long as the apparatus performs lesion detection by using CADe, and the same effects can be obtained.

What is claimed is:
1. A medical image processing apparatus comprising:
an image processing unit configured to process a medical image acquired by a medical image imaging apparatus, wherein
the image processing unit includes a detection unit configured to detect a lesion candidate region from the medical image, and a validity evaluation unit configured to evaluate validity of a detection result of the detection unit,
the validity evaluation unit includes a normal tissue extraction unit configured to extract a normal tissue region from the medical image by using position information of the lesion candidate region detected by the detection unit, and a feature extraction unit configured to calculate a variation feature amount indicating a difference between features of the lesion candidate region and the normal tissue region, and evaluates validity of the detection result by using the variation feature amount calculated by the feature extraction unit.

2. The medical image processing apparatus according to claim 1, wherein
the normal tissue extraction unit extracts a region adjacent to the lesion candidate region as the normal tissue region.

3. The medical image processing apparatus according to claim 1, wherein
the normal tissue extraction unit extracts a region adjacent to the lesion candidate region in a horizontal direction as the normal tissue region.

4. The medical image processing apparatus according to claim 1, wherein
the validity evaluation unit includes a layer structure analysis unit configured to analyze inclination in a horizontal direction with respect to the normal tissue region extracted by the normal tissue extraction unit, and
the normal tissue extraction unit corrects the normal tissue region by using the inclination acquired by the layer structure analysis unit, and passes the corrected normal tissue region to the feature extraction unit.

5. The medical image processing apparatus according to claim 1, wherein
the validity evaluation unit includes a lower layer portion region extraction unit configured to extract regions below the lesion candidate region detected by the detection unit and the normal tissue region extracted by the normal tissue extraction unit, and a lower layer portion region feature extraction unit configured to calculate a lower layer portion variation feature amount indicating a difference in features between a lower layer of the lesion candidate region and a lower layer of the normal tissue region for the lower layer portion region extracted by the lower layer portion region extraction unit, and evaluates validity of the detection result by using the lower layer portion variation feature amount.

6. The medical image processing apparatus according to claim 1, wherein
the feature extraction unit divides each of the lesion candidate region and the normal tissue region into small regions, calculates a set or a vector indicating a feature of each small region, and calculates the variation feature amount based on a similarity between a set or a vector calculated for the lesion candidate region and a set or a vector calculated for the normal tissue region.

7. The medical image processing apparatus according to claim 1, wherein
the medical image is an ultrasonic image acquired by an ultrasonic imaging apparatus.

8. The medical image processing apparatus according to claim 7, wherein
the feature extraction unit extracts features of the lesion candidate region and the normal tissue region by using a difference in the ultrasonic images between frames.

9. The medical image processing apparatus according to claim 1, wherein
the validity evaluation unit further includes a lesion candidate region extraction unit configured to extract a lesion candidate region based on a detection result of the detection unit.

10. The medical image processing apparatus according to claim 9, wherein
the lesion candidate region extraction unit compares detection results of medical images acquired temporally before and after, and changes an evaluation criterion for evaluating validity.

11. The medical image processing apparatus according to claim 1, wherein
the feature extraction unit calculates the variation feature amount by using one or more of luminance of the medical image, a difference between time-series images, an edge feature, a texture feature, a frequency feature in combination.

12. The medical image processing apparatus according to claim 1, wherein
the detection unit includes a convolutional neural network including a large number of convolution processes, and outputs position information and a certainty factor of a detection result of a detected lesion candidate region detected by the convolutional neural network.

13. The medical image processing apparatus according to claim 12, wherein
the validity evaluation unit evaluates validity of the detection result by using the certainty factor output by the detection unit together with the variation feature amount.

14. The medical image processing apparatus according to claim 1, further comprising:
a display control unit configured to display an evaluation result of the validity evaluation unit on a display device, wherein
the display control unit displays the evaluation result obtained by the validity evaluation unit together with the detection result obtained by the detection unit.

15. A medical imaging apparatus comprising:
an imaging unit configured to acquire a medical image of a subject; and
an image processing unit configured to process the medical image acquired by the imaging unit, wherein
the image processing unit includes a detection unit configured to detect a lesion candidate region from the medical image, and a validity evaluation unit configured to evaluate validity of a detection result of the detection unit,
the validity evaluation unit includes a normal tissue extraction unit configured to extract a normal tissue region from the medical image by using position information of the lesion candidate region detected by the detection unit, and a feature extraction unit configured to calculate a variation feature amount indicating a difference between features of the lesion candidate region and the normal tissue region, and evaluates validity of the detection result by using the variation feature amount calculated by the feature extraction unit.

* * * * *